(12) United States Patent
Cardonha et al.

(10) Patent No.: US 8,812,243 B2
(45) Date of Patent: Aug. 19, 2014

(54) TRANSMISSION AND COMPRESSION OF GENETIC DATA

(75) Inventors: Carlos H. Cardonha, Sao Paulo (BR); Robert R. Friedlander, Southbury, CT (US); Ricardo G. Herrmann, Sao Paulo (BR); James R. Kraemer, Santa Fe, NM (US); Julio Nogima, Londrina (BR)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/467,292

(22) Filed: May 9, 2012

(65) Prior Publication Data

US 2013/0304391 A1    Nov. 14, 2013

(51) Int. Cl.
*G06F 7/00* (2006.01)
*G06F 19/22* (2011.01)

(52) U.S. Cl.
CPC ..................................... *G06F 19/22* (2013.01)
USPC ............................... 702/19; 703/11; 707/700

(58) Field of Classification Search
CPC ......... G06F 19/22; G06F 19/18; G06F 19/20; G06F 19/24; G06F 19/10; G06F 19/26; G06F 19/28; G06F 19/3443; G06F 17/30; G06F 17/30153; G06F 19/00; G06F 19/16
See application file for complete search history.

(56) References Cited

U.S. PATENT DOCUMENTS

| | | | |
|---|---|---|---|
| 6,401,043 B1 | 6/2002 | Stanton, Jr. | |
| 6,468,744 B1 | 10/2002 | Cronin et al. | |
| 7,017,186 B2 | 3/2006 | Day | |
| 8,012,740 B2 | 9/2011 | Hillis et al. | |
| 8,055,603 B2 | 11/2011 | Angell | |
| 8,126,655 B2 | 2/2012 | Katoh et al. | |
| 8,145,582 B2 | 3/2012 | Angell | |
| 8,296,268 B2 | 10/2012 | Ingles et al. | |
| 8,340,914 B2 | 12/2012 | Gatewood et al. | |
| 2003/0194711 A1 | 10/2003 | Zapala | |
| 2003/0195706 A1 | 10/2003 | Korenberg | |
| 2003/0220844 A1 | 11/2003 | Marnellos | |
| 2004/0153255 A1 | 8/2004 | Ahn | |
| 2004/0224334 A1 | 11/2004 | Shibuya | |
| 2005/0019787 A1 | 1/2005 | Berno et al. | |
| 2005/0267693 A1 | 12/2005 | Allard et al. | |
| 2006/0112264 A1 | 5/2006 | Agarwal | |
| 2006/0166224 A1 | 7/2006 | Norviel | |
| 2007/0276610 A1 | 11/2007 | Korenberg | |
| 2008/0294692 A1 | 11/2008 | Angell et al. | |
| 2009/0006002 A1 | 1/2009 | Honisch et al. | |
| 2009/0182862 A1 | 7/2009 | Thomson et al. | |
| 2010/0241670 A1 | 9/2010 | Justice et al. | |
| 2011/0087436 A1 | 4/2011 | Klapa et al. | |
| 2011/0319298 A1 | 12/2011 | Benner et al. | |
| 2012/0066001 A1 | 3/2012 | Sanborn | |
| 2012/0197533 A1 | 8/2012 | Nazarenko | |
| 2012/0230326 A1* | 9/2012 | Ganeshalingam et al. | ... 370/389 |

FOREIGN PATENT DOCUMENTS

| | | |
|---|---|---|
| CN | 101430742 A | 5/2009 |
| CN | 102081707 A | 6/2011 |
| CN | 102222174 A | 10/2011 |
| JP | 2004240975 | 8/2004 |
| WO | 02063479 A1 | 8/2002 |
| WO | 03081509 A2 | 10/2003 |
| WO | 03083442 A2 | 10/2003 |
| WO | 2005107412 A2 | 11/2005 |
| WO | 2010072382 A2 | 7/2010 |
| WO | 2011076130 A1 | 6/2011 |

OTHER PUBLICATIONS

International HapMap Project; http://hapmap.ncbi.nlm.nih.gov/cgi-perl/gbrowse/hapmap27_B36/; Feb. 2009; 2 pages.
International HapMap Project: http://en.wikipedia.org/wiki/International_HapMap_Project; Oct. 27, 2002; 4 pages.
Hoffmann K. et al.; "easyLINKAGE-Plus—automated linkage analyses using large-scale SNP data"; BioInformatics Applications Note, vol. 21 No. 17 2005. pp. 3565-3567.
Christley, S. et al., "Human genomes as email attachments"; Bio Informatics—vol. 25; 2009; pp. 274-275.
Brandon, M.G. et al., "Data structures and compression algorithms for genomic sequence data"; BioInformatics—vol. 25: 2009; pp. 1731-1738.
Cao, M.D. et al.: "A genome alignment algorithm based on compression"; BMC Cioinformatics; 2010; 16 pages.
He, Q. et al; A Variable Selection Method for Genome-Wide Association Studies; Dept. of Biostatistics, Univ. of North Carolina; Oct. 2010; pp. 1-8.

(Continued)

*Primary Examiner* — Mary Zeman
(74) *Attorney, Agent, or Firm* — Brown & Michaels, PC; John R. Pivnichny (57) ABSTRACT

A method, computer product and computer system of transmitting a compressed genome of an organism: a computer at a source reading an uncompressed sequence and a reference genome from a repository; the computer comparing nucleotides of the genetic sequence of the organism to nucleotides from a reference genome, to find differences where nucleotides of the genetic sequence of the organism which are different from the nucleotides of the reference genome; the computer using the differences to create surprisal data, the surprisal data comprising a starting location of the differences within the reference genome, and the nucleotides from the genetic sequence of the organism which are different from the nucleotides of the reference genome; and the computer transmitting, to a destination, a compressed genome comprising: surprisal data and an indication of the reference genome, discarding sequences of nucleotides that are the same in the sequence of the organism and reference genome.

19 Claims, 6 Drawing Sheets

(56) References Cited

OTHER PUBLICATIONS

Ruschendorf, F. et al.; "ALOHOMORA: a tool for linkage analysis using 10K SNP Array Data"; BioInformatics Applications Note; vol. 21, No. 9, 2005; pp. 2123-2125.
Wacker, S.A. et al.; "Using transcriptome sequencing to identify mechanisms of drug action and resistance"; Nature Chemical Biology; 2012; 37 pages.
PCT Search Report for PCT/IB2013/052012 mailed Aug. 15, 2013; 10 pages.
Craig, A.G. et al; "Ordering of cosmid clones covering the Herpes simplex virus type 1 (HSV-1) genome: a test case for fingerprinting by hybridisation"; Nucleic Acids Research, vol. 18, No. 9; 1990; pp. 2653-2660.
Hillman-Jackson, J. et al; "Using Galaxy to Perform Large-Scale Interactive Data Analyses"; Current Protocols in Bioinformatics, Jun. 2012; 47 pages.
Galaxy Wiki; http://wiki.g2.bx.psu.edu/; At least as early as 2011; 2 pages.
Galaxy Wiki; "Custom Genomes"; http://wiki.g2.bx.psu.edu/Learn/CustomGenomes; At least as early as Apr. 2012; 4 pages.
Galaxy—Rous; "Comparing genomic intervals using galaxy"; http://rous.mit.edu/index.php/Comparing_genomic_intervals_using_galaxy; At least as early as Jan. 27, 2010; 2 pages.
The Galaxy Team; "An Introduction to Galaxy"; http://UseGalaxy.org; Jul. 28, 2011; 107 pages.
Christopher Schmid; "Reviews in Computational Biology Comparing Epigenetic Maps: Computational tasks and aspects of data analysis"; Swiss Tropical and Public Health Institute; May 2, 2011; 31 pages.
Centroid definition , "The Penguin Dictionary of Mathematics" 2008.
Kohane, I et al.; "Health Information Identification and De-Identification Toolkit"; Proc AMIA Symp.; 1998; pp. 356-360.
Malin, B.; "An Evaluation of the Current State of Genomic Data Privacy Protection Technology and a Roadmap for the Future"; J Am Med Inform Assoc.; Dec. 2005; pp. 28-34.
Kapis, K. et al.; "Security Mechanisms for Electronic Patient Records in Mobile Intelligent Services"; MEDINF; Craiova Medicala Journal; Oct. 2003; 4 Pages.
Heurix, J. et al.; "A Hybrid Approach Integrating Encryption and Pseudonymization for Protecting Electronic Health Records"; Proceedings of the Eighth IASTED International Conference on Biomedical Engineering; 2011; 8 pages.
Weerasinghe, D. et al.; "Securing electronic health records with novel mobile encryption schemes"; Int. J. Electronic Healthcare; 2007, vol. 3 No. 4; pp. 395-416.
Dean, J. et al; MapReduce: Simplified Data Processing on Large Clusters; OSDI; 2004; pp. 1-13.
Hedlund, B.; Understanding Hadoop Clusters and the Network; http://bradhedlund.com/?p=3108; Sep. 10, 2011; 26 pages.
Titmus, M. et al.; Answering the demands of digital genomics; Concurrency and Computation: Practice and Experience; Aug. 2012; 12 pages.
Schadt, E. et al.; Computational solutions to large-scale data management and analysis; Nat. Rev. Genet; Sep. 2010; 22 pages.
Shvachko, K. et al.; The Hadoop Distributed File System; IEEE; 2010: 10 pages.
ssahaSNP: Sequence Search and Alignment by Hashing Algorithm; http://www.sanger.ac.uk/resources/software/ssahashp/; Wellcome Trust Sanger Institute; 2011; 2 pages.
GWASelect: A Variable Selection Method for Genomewide Association Studies ; http://www.bios.unc.edu/~lin/software/GWASelect; at least as early as Feb. 23, 2010; 1 page.
Jorde, L. B. et al.; Genetic variation, classification and 'race'; 2004; Nature Genetics 36 (11 Suppl): S28-S33; 8 pages.
Tishkoff, S. A. et al., Implications of biogeography of human populations for 'race' and medicine; Nature Genetics 36 (11 Suppl): S21-7; 2004; 9 pages.
International HapMap Project; http://hapmap.ncbi.nlm.nih.gov/; 2009; 3 pages.
Human Genome Project Information; http://www.ornl.gov/sci/techresources/Human_Genome/fag/fags1.shtml; 1990; 9 pages.
Human Genome Diversity Project; http://wikipedia.org/wiki/Human_Genome_Diversity_Project; 2012; 5 pages.
Cavalli-Sforza, L., "The Human Genome Diversity Project: past, present and future";Nature Reviews/Genetics; Apr. 2005; 8 pages.
Rosenberg, N.A.; "Standardized subsets of the HGDP-CEPH Human Genome Diversity Cell Llne Panel, accounting for atypical and duplicated samples and pairs of close relatives"; Annals of Human Genetics; Feb. 2006; 40 pages.
Amigo, J. et al.; SPSmart: adapting population based SNP genotype databases for fast and comprehensive web access; BMC Bioinformatics; Oct. 2008; 6 pages.
Li, J.A. et al; "Worldwide Human Relationships Inferred from Genome-Wide Patterns of Variation"; Science—vol. 319; 2008; 6 pages.
Novembre, J. et al., "Genes mirror geography within Europe"; Nature; Nov. 2008; 13 pages.
Grumbach, S. et al.; A New Challenge for Compression Algorithms: Genetic Sequences; Genetic Sequences; 1994;12 pages.
International PCT Search Report for PCT/IB2013/052011; Jun. 18, 2013; 8 pages.
International PCT Search Report for PCT/IB2013/055173; Jan. 2, 2014; 9 pages.
Haefliger et al. "Four Novel Members of the Connexin Family of Gap Junction Proteins." The Journal of Biological Chemistry. Vol. 267, 1992, pp. 2057-2064.

\* cited by examiner

Organism sequence: ...TAGCAATGA...
                        ^
                       485

Reference genome sequence: ...TAGGTTAGA...
                                ^
                               485

Surprisal Data: location of difference: 485
number of different nucleic acid bases: 4
actual changed nucleic acid bases: CAAT

Fig. 6

Reference genome sequence: ...TAGGTTAGA...
                                ^
                               485
                                +
Surprisal Data: location of difference: 485
number of different nucleic acid bases: 4
actual changed nucleic acid bases: CAAT Organism's complete genome: ...TAGCAATGA...
                                  ^
                                 485

Fig. 7

TRANSMISSION AND COMPRESSION OF GENETIC DATA

BACKGROUND

The present invention relates to transmission of genetic data, and more specifically to transmission and compression of genetic data.

DNA gene sequencing of a human, for example, generates about 3 billion ($3 \times 10^9$) nucleotide bases. Currently all 3 billion nucleotide base pairs are transmitted, stored and analyzed, with each base pair typically represented as two bits. The storage of the data associated with the sequencing is significantly large, requiring at least 3 gigabytes of computer data storage space to store the entire genome which includes only nucleotide sequenced data and no other data or information such as annotations. If the entire genome included other information, such as annotations, the genome may require terabytes worth of storage. The movement of the data between institutions, laboratories and research facilities is hindered by the significantly large amount of data, the significant amount of storage necessary to contain the data, and the resources necessary to directly transmit the data. For example, some research facilities can spend upwards of $2 million dollars for transmitting genetic data and sending genetic data that is large, for example terabytes of data that includes annotations and specifics regarding the genetic sequence or genome. The transfer of genetic sequence that is very large can take a significant amount of time over a network data processing system.

Figure 2:
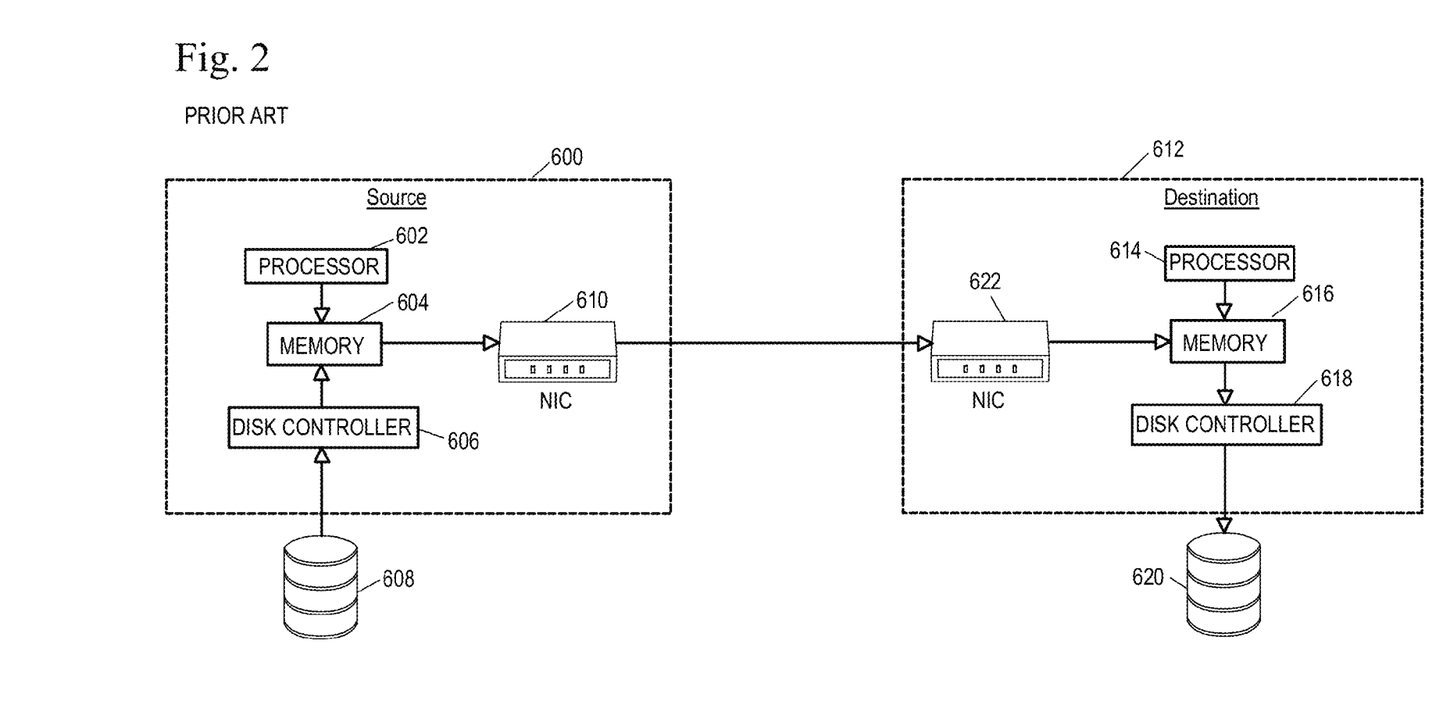
FIG. 2 an overview of a conventional transmission system between a source and a destination of a genome for transmission.

FIG. 2 shows an overview of conventional transmission between a source and a destination of a genome. An uncompressed genome at a source 600 is read from a repository 606 by a disk controller 606. The uncompressed genome is then moved to memory 604. A processor 602 runs an algorithm to compress the genome. An output from the processor 602 of a compressed genome is then sent to a network interface controller (NIC) 610. The NIC controller 610 of the source 600 sends the compressed genome through a network to a NIC 622 at a destination 612. The compressed genome that was received by the NIC 622 at the destination 612 is sent to memory 616. A processor 614 at the destination 612 then runs an algorithm to decompress the compressed genome and stores the decompressed genome to memory 616. From memory 616, the decompressed genome is moved to a repository 620 by a disk controller 618 at the destination 612.

SUMMARY

According to one embodiment of the present invention, a method of transmitting a compressed genome of an organism. The method comprising the steps of: a computer at a source reading an uncompressed sequence and a reference genome from a repository; the computer comparing nucleotides of the genetic sequence of the organism to nucleotides from a reference genome, to find differences where nucleotides of the genetic sequence of the organism which are different from the nucleotides of the reference genome; the computer using the differences to create surprisal data, the surprisal data comprising a starting location of the differences within the reference genome, and the nucleotides from the genetic sequence of the organism which are different from the nucleotides of the reference genome; the computer transmitting, to a destination, a compressed genome comprising: the surprisal data and an indication of the reference genome, discarding sequences of nucleotides that are the same in the genetic sequence of the organism and the reference genome.

According to another embodiment of the present invention, a method of receiving a compressed genome of an organism. The method comprising the steps of: a computer receiving a compressed genome from a source, the compressed genome comprising surprisal data comprising a starting location of the differences within the reference genome, and the nucleotides from the genetic sequence of the organism which are different from the nucleotides of the reference genome, and an indication of the reference genome used to compress the genome; the computer retrieving the indicated reference genome from a repository; and the computer altering the reference genome based on the surprisal data by replacing nucleotides at each location in the reference genome specified by the surprisal data with the nucleotides from the genetic sequence of the organism in the surprisal data associated with the location; resulting in an entire genome of the organism.

According to another embodiment of the present invention, a system for transmitting genetic surprisal data of a genome of an organism from a source to a destination. The system comprising: a first compression device at the source comprising: one or more processors with a plurality of inputs and outputs, wherein at least one input is connected to one or more computer-readable, tangible storage devices for receiving an uncompressed sequence of the organism and a reference genome and at least one output is connected to a network interface controller for outputting a compressed sequence of the organism comprising surprisal data; one or more computer-readable memories coupled to one of the plurality of inputs of the one or more processors; program instructions, stored on at least one of the one or more storage devices for execution by at least one of the one or more processors via at least one of the one or more memories, to compare nucleotides of the genetic sequence of the organism to nucleotides from a reference genome, to find differences where nucleotides of the genetic sequence of the organism which are different from the nucleotides of the reference genome; program instructions, stored on at least one of the one or more storage devices for execution by at least one of the one or more processors via at least one of the one or more memories, to use the differences to create surprisal data, the surprisal data comprising a starting location of the differences within the reference genome, and the nucleotides from the genetic sequence of the organism which are different from the nucleotides of the reference genome; program instructions, stored on at least one of the one or more storage devices for execution by at least one of the one or more processors via at least one of the one or more memories, to transmit, to a destination, a compressed genome comprising: the surprisal data and an indication of the reference genome, and discarding sequences of nucleotides that are the same in the genetic sequence of the organism and the reference genome. The system also comprising: a second compression device at the destination coupled to the first compression device at the source through a network comprising: one or more processors with a plurality of inputs and outputs, wherein at least one input is connected to network interface controller for receiving a compressed sequence of the organism and at least one output is connected to one or more computer-readable, tangible storage devices for outputting an entire genome of the organism; one or more computer-readable memories coupled to one of the plurality of inputs; program instructions, stored on at least one of the one or more storage devices for execution by at least one of the one or more processors via at least one of the one or more memories, to receive a compressed genome from a source, the compressed genome comprising surprisal data and an indication of the reference genome used to compress the genome; program instructions, stored on at least one of the one or more storage devices for execution by at least one of the one or more processors via at least one of the one or more memories, to retrieve the indicated reference genome from a repository; and program instructions, stored on at least one of the one or more storage devices for execution by at least one of the one or more processors via at least one of the one or more memories, to alter the reference genome based on the surprisal data by replacing nucleotides at each location in the reference genome specified by the surprisal data with the nucleotides from the genetic sequence of the organism in the surprisal data associated with the location; resulting in an entire genome of the organism.

According to another embodiment of the present invention, a device for transmitting genetic surprisal data of a genome of an organism from a source to a destination. The device comprising: one or more processors with a plurality of inputs and outputs, wherein at least one input is connected to one or more computer-readable, tangible storage devices for receiving an uncompressed sequence of the organism and a reference genome and at least one output is connected to a network interface controller for outputting a compressed sequence of the organism comprising surprisal data; one or more computer-readable memories coupled to one of the plurality of inputs of the one or more processors; program instructions, stored on at least one of the one or more storage devices for execution by at least one of the one or more processors via at least one of the one or more memories, to compare nucleotides of the genetic sequence of the organism to nucleotides from a reference genome, to find differences where nucleotides of the genetic sequence of the organism which are different from the nucleotides of the reference genome; program instructions, stored on at least one of the one or more storage devices for execution by at least one of the one or more processors via at least one of the one or more memories, to use the differences to create surprisal data, the surprisal data comprising a starting location of the differences within the reference genome, and the nucleotides from the genetic sequence of the organism which are different from the nucleotides of the reference genome; and program instructions, stored on at least one of the one or more storage devices for execution by at least one of the one or more processors via at least one of the one or more memories, to transmit, to a destination, a compressed genome comprising: the surprisal data and an indication of the reference genome, and discarding sequences of nucleotides that are the same in the genetic sequence of the organism and the reference genome.

According to another embodiment of the present invention, a device at a destination for receiving genetic surprisal data of a genome of an organism from a source. The device comprising: one or more processors with a plurality of inputs and outputs, wherein at least one input is connected to network interface controller for receiving a compressed sequence of the organism and at least one output is connected to one or more computer-readable, tangible storage devices for outputting an entire genome of the organism; one or more computer-readable memories coupled to one of the plurality of inputs; program instructions, stored on at least one of the one or more storage devices for execution by at least one of the one or more processors via at least one of the one or more memories, to receive a compressed genome from a source, the compressed genome comprising surprisal data and an indication of the reference genome used to compress the genome; program instructions, stored on at least one of the one or more storage devices for execution by at least one of the one or more processors via at least one of the one or more memories, to retrieve the indicated reference genome from a repository; and program instructions, stored on at least one of the one or more storage devices for execution by at least one of the one or more processors via at least one of the one or more memories, to alter the reference genome based on the surprisal data by replacing nucleotides at each location in the reference genome specified by the surprisal data with the nucleotides from the genetic sequence of the organism in the surprisal data associated with the location; resulting in an entire genome of the organism.

DETAILED DESCRIPTION

The illustrative embodiments of the present invention recognize that the difference between the genetic sequence from two humans is about 0.1%, which is one nucleotide difference per 1000 base pairs or approximately 3 million nucleotide differences. The difference may be a single nucleotide polymorphism (SNP) (a DNA sequence variation occurring when a single nucleotide in the genome differs between members of a biological species), or the difference might involve a sequence of several nucleotides. The illustrative embodiments recognize that most SNPs are neutral but some, 3-5% are functional and influence phenotypic differences between species through alleles. Furthermore that approximately 10 to 30 million SNPs exist in the human population of which at least 1% are functional. The illustrative embodiments also recognize that with the small amount of differences present between the genetic sequence from two humans, the "common" or "normally expected" sequences of nucleotides can be compressed out or removed to arrive at "surprisal data"- differences of nucleotides which are "unlikely" or "surprising" relative to the common sequences. The dimensionality of the data reduction that occurs by removing the "common" sequences is $10^3$, such that the number of data items and, more important, the interaction between nucleotides, is also reduced by a factor of approximately $10^3$—that is, to a total number of nucleotides remaining is on the order of $10^3$. The illustrative embodiments also recognize that by identifying what sequences are "common" or provide a "normally expected" value within a genome, and knowing what data is "surprising" or provides an "unexpected value" relative to the normally expected value, the only data needed to recreate the entire genome in a lossless manner is the surprisal data and the genome used to obtain the surprisal data.

The illustrative embodiment of the present invention also recognizes that by specifically using a device that can compress or decompress a sequence or genome as data is transferred to the device and outputs either a compressed genome or an entire genome of an organism without storing the data in memory, significantly reduces resources used to transfer data between a source and a destination.

Figure 1:
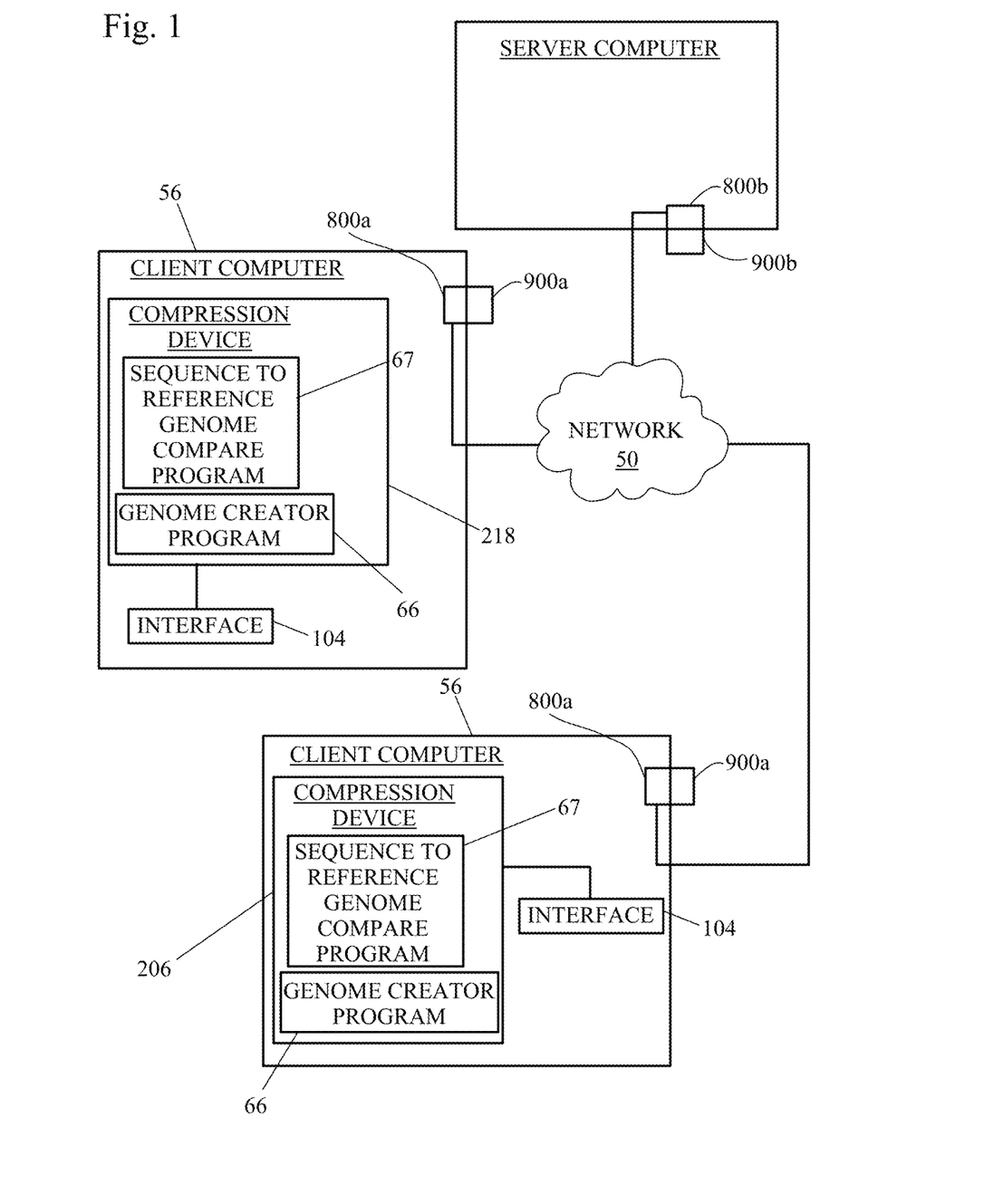
FIG. 1 shows depicts an exemplary diagram of a possible data processing environment in which illustrative embodiments may be implemented.

FIG. 1 is an exemplary diagram of a possible data processing environment provided in which illustrative embodiments may be implemented. It should be appreciated that FIG. 1 is only exemplary and is not intended to assert or imply any limitation with regard to the environments in which different embodiments may be implemented. Many modifications to the depicted environments may be made.

Referring to FIG. 1, network data processing system 51 is a network of computers in which illustrative embodiments may be implemented. Network data processing system 51 contains network 50, which is the medium used to provide communication links between various devices and computers connected together within network data processing system 51. Network 50 may include connections, such as wire, wireless communication links, or fiber optic cables.

In the depicted example, a client computer 52, another client computer 56, and server computer 54 connect to network 50. In other exemplary embodiments, network data processing system 51 may include additional client computers, storage devices, server computers, and other devices not shown. The client computers 52, 56 include a set of internal components 800a and a set of external components 900a, further illustrated in FIG. 7. The client computers 52, 56 may be, for example, a mobile device, a cell phone, a personal digital assistant, a netbook, a laptop computer, a tablet computer, a desktop computer, a sequencing machine or any other type of computing device.

Client computers 52, 56 may contain an interface 104. The interface can be, for example, a command line interface, a graphical user interface (GUI), or a web user interface (WUI). The interface may be used, for example for viewing an uncompressed sequence from a repository or an entire genome from a repository. A compression device 206, 218 (FIG. 4) may also contain an interface 201, 223 and may be used, for example to instruct the transmission of a compressed genome or receival of a compressed genome.

In the depicted example, server computer 54 provides information, such as boot files, operating system images, and applications to client computers 52, 56. Server computer 54 can compute the information locally or extract the information from other computers on network 50. Server computer 54 includes a set of internal components 800b and a set of external components 900b illustrated in FIG. 7.

Figure 7:
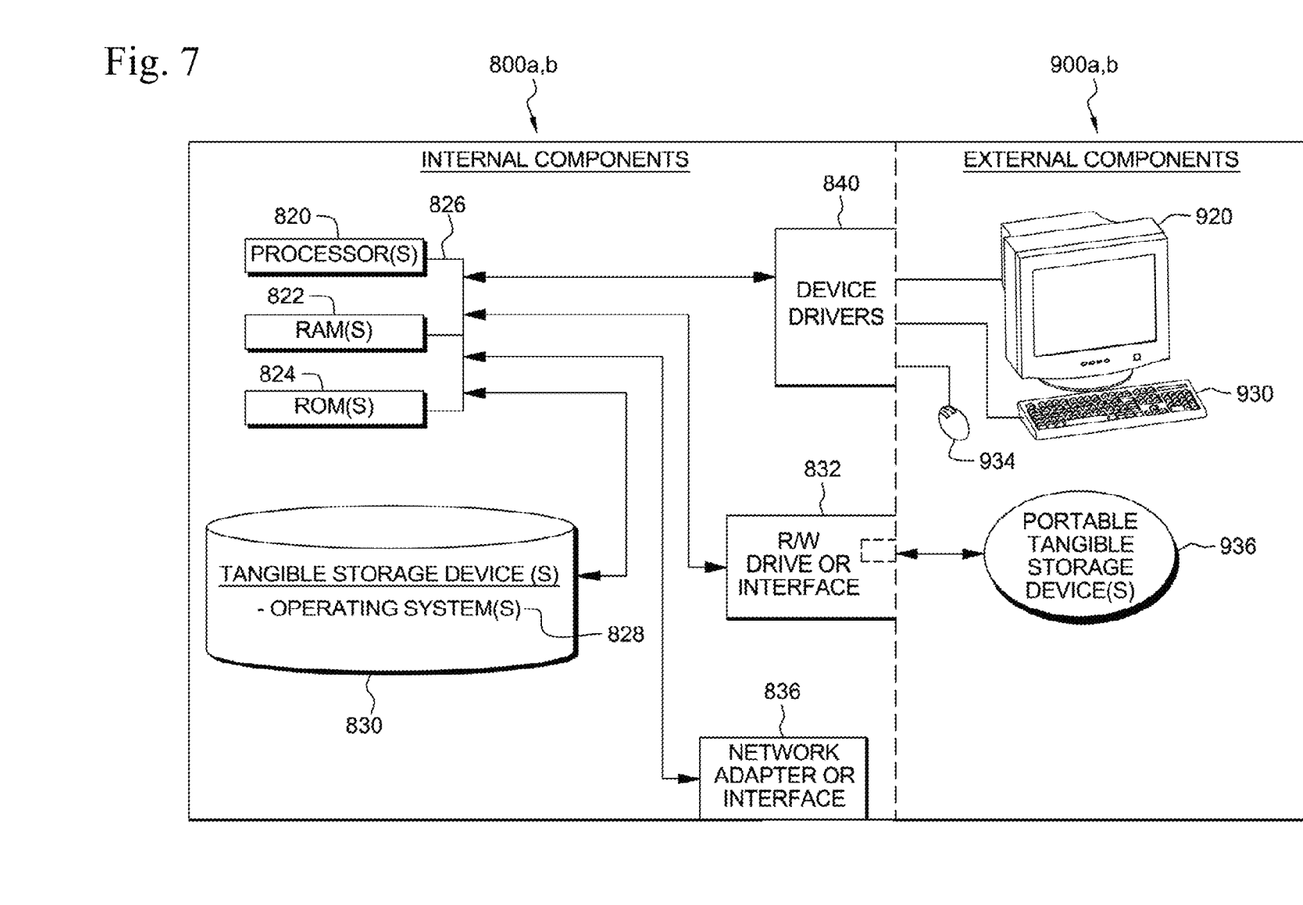
FIG. 7 shows illustrates internal and external components of a client computer and a server computer in which illustrative embodiments may be implemented.

Program code, reference genomes, and programs such as a sequence to reference genome compare program 67 and/or a genome creator program 66 may be stored on at least one of one or more computer-readable tangible storage devices 830 shown in FIG. 7, on at least one of one or more portable computer-readable tangible storage devices 936 as shown in FIG. 7, or repositories 208, 220 (shown in FIG. 4) connected to network 50, or downloaded to a data processing system or other device for use. For example, program code, reference genomes, and programs such as a sequence to reference genome compare program 67 and/or a genome creator program 66 may be stored on at least one of one or more tangible storage devices 830 on server computer 54 and downloaded to client computers 52, 56 over network 50 for use on client computers 52, 54. Alternatively, server computer 54 can be a web server, and the program code, reference genomes, and programs such as a sequence to reference genome compare program 67 and/or a genome creator program 66 may be stored on at least one of the one or more tangible storage devices 830 on server computer 54 and accessed on client computers 52, 56. Sequence to reference genome compare program 67 and/or genome creator program 66 can be accessed on client computers 52, 56 through interface 104. In other exemplary embodiments, the program code, reference genomes, and programs such as sequence to reference genome compare program 67 and genome creator program 66 may be stored on at least one of one or more computer-readable tangible storage devices 830 on client computers 52, 56 or distributed between two or more servers.

Figure 4:
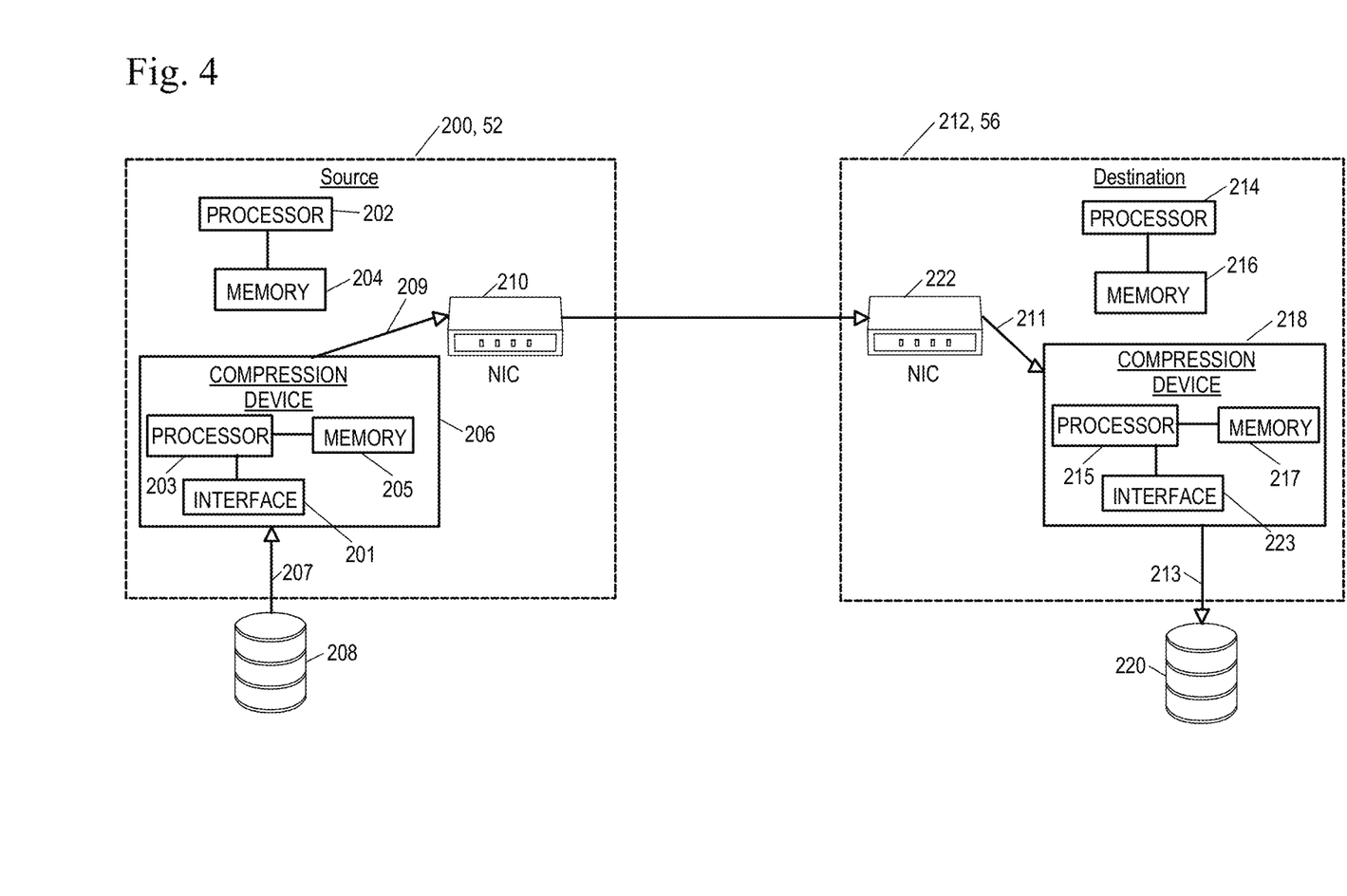
FIG. 4 shows an overview of a transmission system for transmitting a genome between a source and a destination according to an illustrative embodiment.

FIG. 4 shows an overview of a transmission system for transmitting genetic data between a source and a destination according to an illustrative embodiment. In one embodiment, a source 200, for example client computer 52 as shown in FIG. 1, has a processor 202 coupled to memory 204, a compression device 206, and a network interface controller (NIC) 210. The source 200 is connected to a repository 208, for example, through a network.

The compression device 206 at source 200 includes an input 207 coupled to a processor 203, memory 205 coupled to an input of the processor 203, and an output 209 coupled to the processor 203. The processor 203 may also have an input from an interface.

Information regarding where a compressed sequence is to be sent, what reference genome is to be used, identification of the sample and other administrative functions may be directed by the processor 202 of the source 200 through an interface, for example interface 104 of FIG. 1 or may be directed by the processor 203 of the compression device through interface 201.

The input 207 of the processor of the compression device 206 receives an uncompressed sequence or genome of an organism and a reference genome from repository 208. The output 209 of the compression device 206 outputs a compressed sequence to a network interface controller (NIC) 210 as the compressed sequence is generated by the processor 203 of the first compression device 206. The compressed sequence is removed from the memory 205 of the compression device 206 once the compressed sequence has been outputted 209 from the compression device. It should be noted that during the actual compression of the genome of an organism, the processor 202 and memory 204 of the source 200 are not used.

The uncompressed sequence may be a DNA sequence, an RNA sequence, or a nucleotide sequence and may represent a sequence or a genome of an organism. The organism may be a fungus, microorganism, human, animal or plant.

The reference genome is a digital nucleic acid sequence database which includes numerous sequences. The sequences of the reference genome do not represent any one specific individual's genome, but serve as a starting point for broad comparisons across a specific species, since the basic set of genes and genomic regulator regions that control the development and maintenance of the biological structure and processes are all essentially the same within a species. In other words, the reference genome is a representative example of a species' set of genes.

The compressed sequence includes surprisal data and an indication identifying the reference genome used. The compressed sequence is indicative of an organism's genome regardless of whether the reference genome was compared to part of an organism's genome, for example a partial sequence or an organism's entire genome. The surprisal data is defined as at least one nucleotide difference that provides an "unexpected value" relative to the normally expected value of the reference genome sequence. In other words, the surprisal data contains at least one nucleotide difference present when comparing the sequence to the reference genome sequence. The surprisal data that is sent to the destination 212 preferably includes a location of the difference within the reference genome, the number of nucleic acid bases that are different, and the actual changed nucleic acid bases.

The NIC 210 at the source 200 transmits the compressed sequence to a NIC 222 at a destination 212 through a network, for example network 50 of a network processing system 51 as shown in FIG. 1. The destination 212, for example client computer 56 as shown in FIG. 1, has a processor 214 coupled to memory 216, a compression device 218, and a network interface controller (NIC) 222. The destination 212 is connected to a repository 220, for example, through a network.

The compression device 218 at destination 212 includes an input 211 coupled to a processor 215, memory 217 coupled to an input of the processor 215, and an output 213 coupled to the processor 215. The processor 15 may also have an input from an interface.

Information regarding what reference genome is to be used, identification of the sample and other administrative functions may be directed by the processor 214 of the destination 212 through an interface, for example interface 104 of FIG. 1 or may be directed by the processor 215 of the compression device 218 through interface 223.

The input 211 for the compression device 218 receives a compressed sequence which includes surprisal data and the indication identifying the reference genome used, from the NIC 222. The processor 215 decompresses the compressed sequence and creates an entire, decompressed genome of an organism. The entire, decompressed genome of an organism is outputted 213 to repository 220 as the entire genome of the organism is generated by the processor 215 of the compression device 218.

The decompressed entire genome of the organism is removed from memory 217 of the compression device 218 once the decompressed entire genome of the organism has been outputted 213 from the compression device 218. It should be noted that during the actual decompression of the genome processor 214 and memory 216 of the destination 212 are not used.

While the network interface controller 210, 222 is shown in FIG. 4 as being a separate device from the compression devices 206, 218, the network interface controller 210,222 may be built into the compression device 206, 218 itself.

While only one output and input are shown for the compression devices 206, 218, the compression devices 206, 218 and processors 203, 215 may have numerous inputs and outputs.

Figure 3:
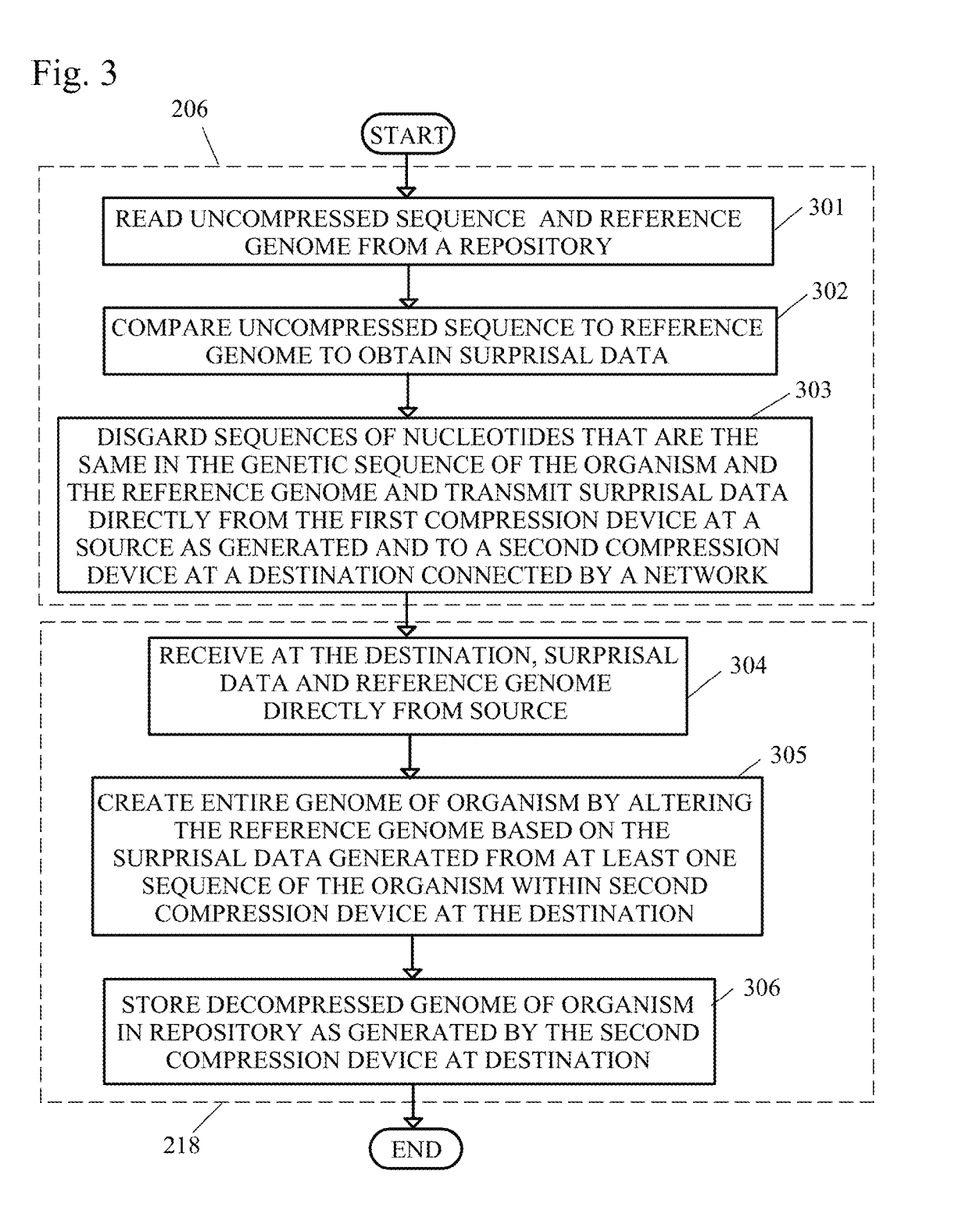
FIG. 3 shows a flowchart of a method of transmission of a genome between a source and a destination according to an illustrative embodiment.

FIG. 3 shows a flowchart of a method of transmission of surprisal data between a source and a destination according to an illustrative embodiment. Steps 301-303 are performed by a first compression device 206 and steps 304-306 are performed by a second compression device. Although, as discussed below, in an alternative embodiment, a compression device may not just be a transmitter or a receiver, but a transceiver in which can both compress sequences and genomes and decompress and create entire genomes of organisms.

In a first step, an uncompressed sequence of an organism and reference sequence are read from a repository 208 (step 301). Repository 208 is not present within the compression device 206, but in communication with the compression device 206, for example, through a network.

A sequence to reference genome compare program 67 within the processor 203 of the first compression device 206 compares the at least one uncompressed sequence to the reference genome to obtain surprisal data (step 302). The surprisal data preferably includes a location of the difference within the reference genome, the number of nucleic acid bases that are different, and the actual changed nucleic acid bases. By including the number of bases which are different within the surprisal data that is compressed, provides a double check of the method by comparing the actual bases to the reference genome bases to confirm that the bases really are different.

Figure 5:
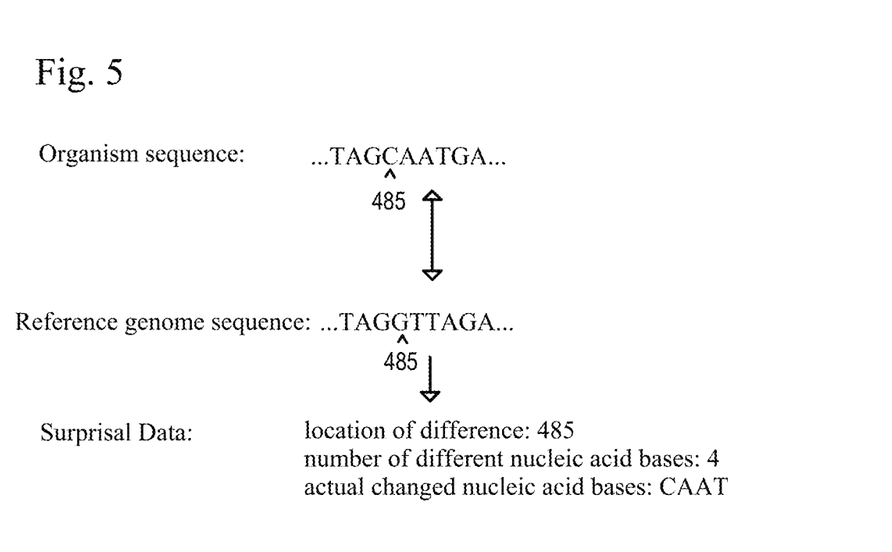
FIG. 5 shows a schematic of the recreation of an organism genome sequence using a reference genome and surprisal data.

FIG. 5 shows a schematic of the comparison of an organism sequence to a reference genome sequence to obtain surprisal data representing an organism's genome. The surprisal data that results from the comparison preferably consists of a location of a difference in the reference genome, the number of bases that were different at the location within the reference genome, and the actual bases that are different than bases in the reference genome at the location. For example, the surprisal data that resulted from comparing the organism sequence to the reference genome shown in FIG. 5 would be surprisal data consisting of: a difference at location 485 of the reference genome; four nucleic acid base differences relative to the reference genome, and the actual bases present in the sequence at the location, for example CAAT (instead of GTTA). The surprisal data and reference genome are stored in memory 205 of the first compression device 206 until the compression device 206 transmits the compressed sequence to the destination 212, for example through a network interface controller 210.

As the surprisal data is generated and the sequence compressed, the sequences of nucleotides that are the same in the genetic sequence of the organism and the reference genome are discarded and the compressed sequence is transmitted directly from the first compression device 206 at a source 200 to a second compression device 218 at a destination 212 (step 303). The transmission may be through a network interface controller 210, 222 that is separate from the compression devices or built into the compression devices.

The compressed sequence is received by a second compression device 218 at a destination 212 (step 304). The compressed sequence may be directly received from the source 200 through an input 211 of the second compression device 218 or transferred from a network interface controller 222 to the input 211 of the second compression device 218. Using the location or index key of the reference genome which was transmitted, a genome creator program 66 can obtain the reference genome from repository 220.

Figure 6:
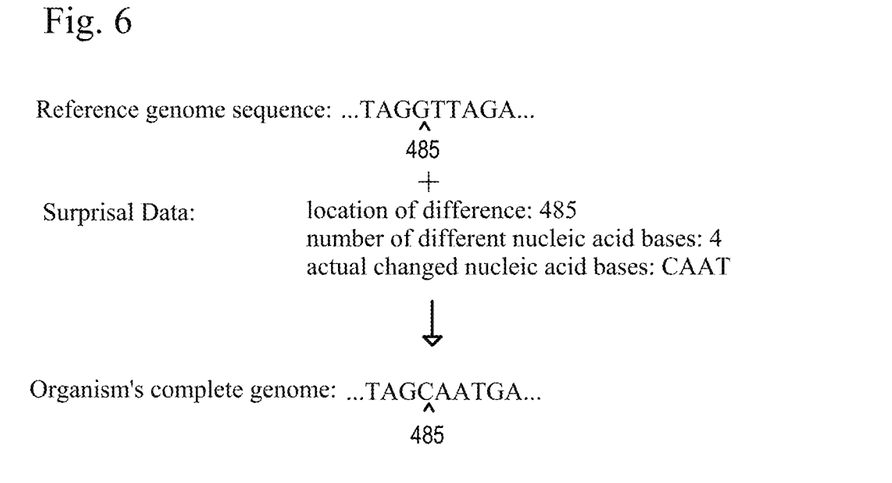
FIG. 6 shows a schematic overview of a method of data surprisal data reduction of genetic data for transmission, storage, and analysis according to an illustrative embodiment.

Using the transmitted reference genome and the surprisal data, the genome creator program 66 (FIG. 1) of the processor 215 of the second compression device 218 finds a location within the reference genome that was indicated as having a difference in the surprisal data and alters the bases of the reference genome to be the bases indicated by the surprisal data. In the example of FIG. 6, based on the surprisal data, a difference is present at location 485, this location is found in the reference genome and GTTA is changed to be CAAT as indicated by the surprisal data. Once all alterations to the reference genome have been made based on the surprisal data, the genome creator program 66 (FIG. 1) of processor 215 of the second compression device 218 then creates an entire genome of an organism by altering the reference genome based on the surprisal data which was generated from a sequence from the organism (step 305) in a lossless manner. The entire decompressed genome of the organism is then stored in a repository 220 in communication with an output 213 of the second compression device 212, for example, through a network (step 306).

The surprisal data may be verified by comparing the nucleotides from the genetic sequence of the organism in the surprisal data to the nucleotides in the reference genome at the location. If all of the nucleotides in the surprisal data are different from the nucleotides in the reference genome the surprisal data is verified. This verification is preferably carried out at the source 200 by the sequence to reference genome compare program 67 prior to transmitting the compressed sequence to a destination 212. If the surprisal data cannot be verified, the processor of the compression device will discard the surprisal data and recreate the compressed sequence to be transmitted.

Alternatively, the verification can be performed by the compression device at the destination during the creation of the entire genome of an organism by a genome creator program 66. If some of the nucleotides in the surprisal data are the same as the nucleotides in the reference genome, the surprisal data has an error. If the surprisal data cannot be verified during creation of the entire genome, the processor of the compression device at the destination will transmit an error message to the source compression device.

While the first compression device 206 was discussed as specifically compressing a sequence, the first compression device 206 may also receive a compressed sequence and decompress the sequence to create an entire genome of an organism, acting as a transceiver. Therefore, all of the steps shown in FIG. 3 could be carried out by the first compression device for different sequences or samples.

Similarly, while the second compression device 218 was discussed as specifically decompressing a sequence, the second compression device 218 may also generate and transmit a compressed sequence, acting as a transceiver. Therefore, all of the steps shown in FIG. 3 could be carried out by the second compression device for different sequences or samples.

It should be noted that in FIGS. 5 and 6, only a portion of both the organism sequence and the reference genome are shown for clarity, and the sequences shown are chosen randomly and do not represent a real DNA sequence of any sort.

FIG. 7 illustrates internal and external components of client computers 52, 56 and server computer 54 in which illustrative embodiments may be implemented. In FIG. 7, client computers 52, 56 and server computer 54 include respective sets of internal components 800a, 800b, and external components 900a, 900b. Each of the sets of internal components 800a, 800b includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828, sequence to reference genome compare program 67 and genome creator program 66 are stored on one or more of the computer-readable tangible storage devices 830 for execution by one or more of the processors 820 via one or more of the RAMs 822 (which typically include cache memory). In the embodiment illustrated in FIG. 7, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800a, 800b also includes a R/W drive or interface 832 to read from and write to one or more portable computer-readable tangible storage devices 936 such as a CD-ROM, DVD, memory stick, magnetic tape, magnetic disk, optical disk or semiconductor storage device. Sequence to reference genome compare program 67 and genome creator program 66 can be stored on one or more of the portable computer-readable tangible storage devices 936, read via R/W drive or interface 832 and loaded into hard drive 830.

Each set of internal components 800a, 800b also includes a network adapter or interface 836 such as a TCP/IP adapter card. Sequence to reference genome compare program 67 or genome creator program 66 can be downloaded to client computers 52, 56 and server computer 54 from an external computer via a network (for example, the Internet, a local area network or other, wide area network) and network adapter or interface 836. From the network adapter or interface 836, sequence to reference genome compare program 67 and genome creator program 66 are loaded into hard drive 830. The network may comprise copper wires, optical fibers, wireless transmission, routers, firewalls, switches, gateway computers and/or edge servers.

Each of the sets of external components 900a, 900b includes a computer display monitor 920, a keyboard 930, and a computer mouse 934. Each of the sets of internal components 800a, 800b also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Sequence to reference genome compare program 67 and genome creator program 66 can be written in various programming languages including low-level, high-level, object-oriented or non object-oriented languages. Alternatively, the functions of a sequence to reference genome compare program 67 and genome creator program 66 can be implemented in whole or in part by computer circuits and other hardware (not shown).

Based on the foregoing, a computer system, method and program product have been disclosed for transmission of surprisal data between a source and destination. However, numerous modifications and substitutions can be made without deviating from the scope of the present invention. Therefore, the present invention has been disclosed by way of example and not limitation.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method of compressing and transmitting an entire genome of an organism, comprising a source computer having one or more processors with a plurality of inputs and outputs and one or more computer-readable memories coupled to one of the plurality of inputs of the one or more processors performing the steps of:

reading an uncompressed genetic sequence representing the entire genome of the organism and a reference genome from a repository;

comparing nucleotides of the genetic sequence representing the entire genome of the organism to nucleotides from a reference genome, to find differences where nucleotides of the genetic sequence of the organism which are different from the nucleotides of the reference genome;

using the differences to create surprisal data, the surprisal data comprising a starting location of the differences within the reference genome, a count of a number of differences at the location within the reference genome, and the nucleotides from the genetic sequence of the organism which are different from the nucleotides of the reference genome;

transmitting, to a destination, an entire genome by sending the surprisal data and an indication of the reference genome and not sending sequences of nucleotides that are the same in the genetic sequence of the organism and the reference genome.

2. The method of claim 1, further comprising receiving the compressed genome of the organism comprising a destination computer having one or more processors with a plurality of inputs and outputs and one or more computer-readable memories coupled to one of the plurality of inputs of the one or more processors performing the steps of:

receiving the compressed genome from the source, the compressed genome comprising surprisal data and an indication of the reference genome used to compress the genome;

retrieving the indicated reference genome from a repository; and altering the reference genome based on the surprisal data by replacing nucleotides at each location in the reference genome specified by the surprisal data with the nucleotides from the genetic sequence of the organism in the surprisal data associated with the location; resulting in an entire genome of the organism.

3. The method of claim 1, wherein the organism is an animal.

4. The method of claim 1, wherein the organism is a microorganism.

5. The method of claim 1, wherein the organism is a plant.

6. The method of claim 1, wherein the organism is a fungus.

7. The method of claim 1, wherein the organism is a human.

8. A system for compressing and transmitting genetic surprisal data of an entire genome of an organism from a source to a destination comprising:

a first compression device at the source comprising:
one or more processors with a plurality of inputs and outputs, wherein at least one input is connected to one or more non-transitory computer-readable storage devices for receiving an uncompressed genetic sequence of the organism and a reference genome and at least one output is connected to a network interface controller for outputting a compressed sequence representing an entire genome of the organism comprising surprisal data;
one or more computer-readable memories coupled to one of the plurality of inputs of the one or more processors;
program instructions, stored on at least one of the one or more storage devices for execution by at least one of the one or more processors via at least one of the one or more memories, to compare nucleotides of the genetic sequence representing the entire genome of the organism to nucleotides from a reference genome, to find differences where nucleotides of the genetic sequence of the organism which are different from the nucleotides of the reference genome;
program instructions, stored on at least one of the one or more storage devices for execution by at least one of the one or more processors via at least one of the one or more memories, to use the differences to create surprisal data, the surprisal data comprising a starting location of the differences within the reference genome, a count of a number of differences at the location within the reference genome, and the nucleotides from the genetic sequence of the organism which are different from the nucleotides of the reference genome;
program instructions, stored on at least one of the one or more storage devices for execution by at least one of the one or more processors via at least one of the one or more memories, to transmit, to a destination, an entire genome by sending the surprisal data and an indication of the reference genome and not sending sequences of nucleotides that are the same in the genetic sequence of the organism and the reference genome;

a second compression device at the destination coupled to the first compression device at the source through a network comprising:
one or more processors with a plurality of inputs and outputs, wherein at least one input is connected to network interface controller for receiving a compressed sequence of the organism and at least one output is connected to one or more non-transitory computer-readable storage devices for outputting an entire genome of the organism;
one or more computer-readable memories coupled to one of the plurality of inputs;
program instructions, stored on at least one of the one or more storage devices for execution by at least one of the one or more processors via at least one of the one or more memories, to receive a compressed genome from a source, the compressed genome comprising surprisal data, a count of a number of differences at the location within the reference genome and an indication of the reference genome used to compress the genome;
program instructions, stored on at least one of the one or more storage devices for execution by at least one of the one or more processors via at least one of the one or more memories, to retrieve the indicated reference genome from a repository; and
program instructions, stored on at least one of the one or more storage devices for execution by at least one of the one or more processors via at least one of the one or more memories, to alter the reference genome based on the surprisal data by replacing nucleotides at each location in the reference genome specified by the surprisal data with the nucleotides from the genetic sequence of the organism in the surprisal data associated with the location; resulting in an entire genome of the organism.

9. The system of claim 8, wherein the organism is an animal.

10. The system of claim 8, wherein the organism is a microorganism.

11. The system of claim 8, wherein the organism is a plant.

12. The system of claim 8, wherein the organism is a fungus.

13. The system of claim 8, wherein the organism is a human.

14. A device for compressing and transmitting genetic surprisal data of an entire genome of an organism from a source to a destination comprising:
one or more processors with a plurality of inputs and outputs, wherein at least one input is connected to one or more non-transitory computer-readable storage devices for receiving an uncompressed genetic sequence of the organism and a reference genome and at least one output is connected to a network interface controller for outputting a compressed sequence representing an entire genome of the organism comprising surprisal data;
one or more computer-readable memories coupled to one of the plurality of inputs of the one or more processors;
program instructions, stored on at least one of the one or more storage devices for execution by at least one of the one or more processors via at least one of the one or more memories, to compare nucleotides of the genetic sequence representing the entire genome of the organism to nucleotides from a reference genome, to find differences where nucleotides of the genetic sequence of the organism which are different from the nucleotides of the reference genome;
program instructions, stored on at least one of the one or more storage devices for execution by at least one of the one or more processors via at least one of the one or more memories, to use the differences to create surprisal data, the surprisal data comprising a starting location of the differences within the reference genome, a count of a number of differences at the location within the reference genome, and the nucleotides from the genetic sequence of the organism which are different from the nucleotides of the reference genome; and program instructions, stored on at least one of the one or more storage devices for execution by at least one of the one or more processors via at least one of the one or more memories, to transmit, to a destination, an entire genome by sending the surprisal data and an indication of the reference genome and not sending sequences of nucleotides that are the same in the genetic sequence of the organism and the reference genome.

15. The device of claim 14, wherein the organism is an animal.

16. The device of claim 14, wherein the organism is a microorganism.

17. The device of claim 14, wherein the organism is a plant.

18. The device of claim 14, wherein the organism is a fungus.

19. The device of claim 14, wherein the organism is a human.

* * * * *